United States Patent [19]

Sota et al.

[11] Patent Number: 4,472,316
[45] Date of Patent: Sep. 18, 1984

[54] 3-BENZOYL-2-MERCAPTOPROPIONIC ACID DERIVATIVES

[75] Inventors: Kaoru Sota, Tokorozawa; Yasuhide Tachi, Toshimaku; Kazuyuki Tomisawa, Saitama; Kazuya Kameo; Toru Matsunaga, both of Ageo; Jiro Sawada, Kodaira, all of Japan

[73] Assignee: Taisho Pharmaceutical Co., Ltd., Japan

[21] Appl. No.: 469,000

[22] Filed: Feb. 23, 1983

[30] Foreign Application Priority Data

Apr. 3, 1982 [JP] Japan .................. 57-34499

[51] Int. Cl.³ .................. C07C 149/43; C07C 153/01
[52] U.S. Cl. .................. 260/455 R; 562/426; 560/15
[58] Field of Search .................. 260/455 B, 455 R; 562/426; 560/15

[56] References Cited

FOREIGN PATENT DOCUMENTS 860303 6/1958 United Kingdom ............ 260/455 R

Primary Examiner—Henry R. Jiles
Assistant Examiner—Robert C. Whittenbaugh
Attorney, Agent, or Firm—Kenway & Jenney

[57] ABSTRACT

Novel compounds having the general formula

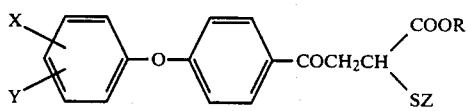

wherein X is hydrogen or halogen, Y is hydrogen, halogen, methoxy or alkyl having 1 to 3 carbon atoms, Z is hydrogen, alkylcarbonyl having 2 to 6 carbon atoms or benzoyl, and R is hydrogen, alkali metal or alkyl having 1 to 5 carbon atoms, are disclosed. These compounds exhibit excellent hypolipidemic activity and little or no side effect.

6 Claims, No Drawings

3-BENZOYL-2-MERCAPTOPROPIONIC ACID DERIVATIVES

The present invention relates to novel 3-Benzoyl-2-mercaptopropionic acid derivatives. More particularly, it relates to 3-benzoyl-2-mercaptopropionic acid derivatives which find utility in the reduction of lipids such as total cholesterols and triglycerides in the blood of mammals.

Generally, sedimentation of excess lipids in blood is considered to be one of causes of arteriosclerosis such as atherosclerosis. Accordingly, therapy of artheriosclerosis and diseases related thereto often involves reduction of lipid concentration in blood.

The present invention is based on the discovery that new 3-benzoyl-2-mercaptopropionic acid derivatives remarkably reduce lipids such as total cholesterols and triglycerides in the blood of mammals and show little or no side effect.

The compounds of the invention are 3-benzoyl-2-mercaptopropionic acid derivatives having the general formula:

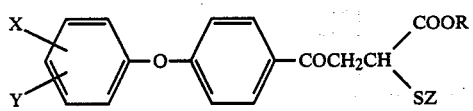
(I)

wherein X is hydrogen or halogen, Y is hydrogen, halogen, methoxy or alkyl having 1 to 3 carbon atoms, Z is hydrogen, alkylcarbonyl having 2 to 6 carbon atoms or benzoyl, and R is hydrogen, alkali metal or alkyl having 1 to 5 carbon atoms.

The term "alkyl" as used throughout the specification, either by itself or as part of a larger group, refers to both straight and branched chain alkyl groups. The term "halogen" refers to fluorine, chlorine, bromine or iodine. X or Y may occur at any position of the phenyl ring.

Preferred compounds of formula I are those wherein X is hydrogen, those wherein Y is hydrogen or halogen, those wherein Z is acetyl, and those wherein R is hydrogen or ethyl.

The compound of formula I may be prepared, for example, by the following methods.

(1) A compound having the general formula:

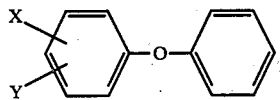

wherein, X and Y are as defined above, is reacted with maleic anhydride in a Friedel-Crafts reaction to give a carboxylic acid compound having the general formula:

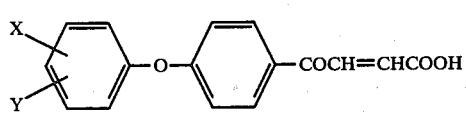
(II)

wherein, X and Y are as defined above.

(2) The compound of formula II is reacted with an alkylating agent having the alkyl group corresponding to R in formula I in the presence of an organic solvent and a base to give an alkyl ester having the general formula:

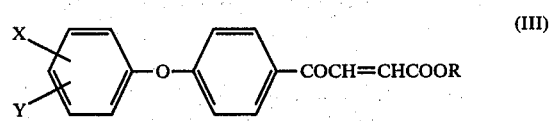
(III)

wherein, X, Y and R are as defined in formula I except that R is other than hydrogen or alkali metal.

Suitable organic solvents include, for example, acetone, dimethylformamide, hexamethylphosphoric triamide and dimethyl sulfoxide.

Suitable bases include, for example, sodium carbonate, potassium carbonate, lithium carbonate, sodium hydrogen-carbonate, potassium hydrogencarbonate, sodium hydroxide, potassium hydroxide, sodium alkoxides and sodium hydride.

Suitable alkylating agents include those conventionally used, such as alkyl halides, dialkyl sulfates, alkyl esters of alkanesulfonic acid(e.g. methanesufonic acid), and alkyl esters of arylsulfonic acid(e.g. p-toluenesulfonic acid).

(3) The compound of formula II or III, dissolved in an organic solvent, is reacted with a thiocarboxylic acid having the general formula: ZSH wherein Z is as defined above other than hydrogen, at a temperature of $-20°$ to $50°$ C. for 0.5 to 24 hours to give the compound of formula I wherein R is hydrogen or alkyl and Z is other than hydrogen.

1 to 2 molar equivalents of the thiocarboxylic acid may be used, relative to the compound of formula II or III.

Suitable organic solvents include, for example, methanol, ethanol, t-butanol, hexane, benzene, toluene, diethyl ether, dimethoxyethane, dioxane, methylene chloride, chloroform, carbon tetrachloride, carbon disulfide, acetone, ethyl acetate, dimethylformamide, hexamethylphosphoric triamide and dimethyl sulfoxide.

(4) The compound of formula I wherein R is alkali metal can be obtained by reacting the compound of formula I wherein R is hydrogen with the same base as used in item (2).

The compound of formula I wherein Z is hydrogen can be obtained by hydrolyzing the compound of formula I wherein Z is alkylcarbonyl or benzoyl, with an acid such as sulfuric acid or hydrochloric acid.

The compound of formula I wherein Z is other than hydrogen can be also obtained by acylating the compound of formula I wherein Z is hydrogen with an acid halide or acid anhydride containing Z which is as defined in formula I other than hydrogen. Examples of the acid halide or acid anhydride are those in which acid moiety is acetic acid, propionic acid, butyric acid, hexanoic acid, benzoic acid or the like.

The compounds of formula I thus obtained can be purified by column chromatography or recrystallization.

(5) Alternatively, the compound of formula II or III may be also prepared by the following method. Namely, a compound having the general formula:

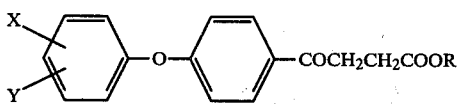

wherein R, X and Y are as defined above, is reacted with bromine in an organic solvent(e.g. diethyl ether, tetrahydrofuran, methylene chloride, chloroform, carbon tetrachloride and the like) to give a compound having the general formula:

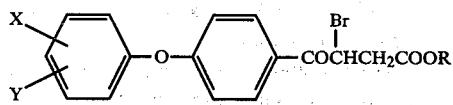

wherein R, X and Y are as defined above, which is then dehydrogenbrominated with a base(e.g. potassium acetate, sodium acetate and the bases are used in item (2)) in an organic solvent(e.g. acetone, ethanol, acetic acid, dimethylformamide, hexamethylphosphoric triamide, dimethyl sulfoxide and the like) to give the compound of formula II or III, i.e. a compound having the general formula:

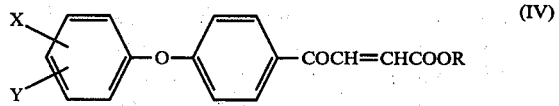

wherein R, X and Y are as defined in formula I.

The starting materials in items (1), (3) and (5), most of which may be known, are conveniently prepared by known methods.

The compounds of the present invention have excellent hypolipidemic activity in mammals such as rat, rabbit and human, and have little or no side effect and, therefore, are useful as hypolipidemic agents. The compound of formula I may be administered orally or parenterally in a conventional dosage form such as tablets, capsules, powders, granules, syrups, and injectionable forms prepared according to conventional pharmaceutical practices.

The effective dosage of the compounds of the present invention depends on the age, weight or response of the patient. Generally, however, the daily dosage in adults may range from 0.1 to 3 g, preferably 0.3 to 1.5 g in single or divided doses.

The following Experiments show the hypolipidemic activity, side effect to liver and toxicity of the compounds of the present invention and a comparative compound, ethyl 2-(4-chlorophenoxy)-2-methylpropionate (hereinafter referred to as "Clofibrate"). The compound number used in these experiments refers to a compound which is prepared in accordance with the hereinafter correspondingly numbered Example.

EXPERIMENT 1

5-Week-old male Wister rats (body weight; 120±6 g, five rats per group) were fed for a week at constant temperature and humidity. At the end of the period, each of the compounds of the present invention and Clofibrate, which was prepared in the form of a suspension of a 5% gum arabic aqueous solution, were orally administered to the rats in a daily dose of 100 mg/kg, as the active ingredient, for 3 consecutive days. A 5% gum arabic aqueous solution was also orally administered to rats for a control group. After administration, each rat was fasted for 18 hours and anesthetized with diethyl ether. Blood was collected through the groin artery and vein, and the lipid concentration in serum was determined with an autoanalizer, and the relative liver weight(g/100 g of body weight) was determined.

Summarized in the following Table are the blood lipid reduction expressed as percentage of the difference of blood lipid concentration between the dosed group and the control group, and the relative liver weight expressed as percentage of the difference in liver weight between the dosed group and the control group.

| Compound | Blood Lipid Reduction (%) | | Liver weight increasing rate (%) |
| --- | --- | --- | --- |
| | Cholesterol | Triglyceride | |
| 1 | 19.2** | 31.7* | 0 |
| 3 | 10.7 | 33.7*** | −1.2 |
| 4 | 10.7 | 22.6* | −1.1 |
| 7 | 53.6*** | 50.4** | 11.9* |
| 13 | 9.9 | 30.1** | 11.1 |
| 14 | 20.7 | 27.6** | 3.5 |
| 16 | 8.5 | 33.4*** | 3.4 |
| 22 | 37.6*** | 21.9 | 12.7 |
| 23 | 41.7*** | 23.9* | 3.5 |
| 27 | 35.8*** | 23.5* | 11.1 |
| 28 | 18.8* | 21.9 | 3.5 |
| Clofibrate | 33.7* | 0.7 | 25.4*** |

Remark:
*p < 0.05,
**p < 0.01,
***p < 0.001

EXPERIMENT 2

Each of 10 ddy male mice (body weight; 22±2 g) was orally administered with Compound 1 in the form of a suspension in a 5% gum arabic aqueous solution. Clofibrate was also administered in the same manner. The animals were observed for 7 days and then the $LD_{50}$ were calculated from the deaths by the Probit method. The $LD_{50}$ values of Compound 1 and Clofibrate were 2.70 g/kg and 0.95 g/kg, respectively.

The following Examples are illustrative of the present invention.

EXAMPLE 1

2.68 g of 3-(4-phenoxybenzoyl)acrylic acid were dissolved in 30 ml of diethyl ether, then 0.8 ml of thioacetic acid was added, and the mixture was stirred for 5 hours. After the diethyl ether was distilled off under reduced pressure, the residue was purified first by silica gel chromatography, eluted with a mixture of hexane and dichloromethane, then by recrystallization from a mixture of hexane and dichloromethane to give 2.96 g of 2-acetylthio-3-(4-phenoxybenzoyl)propionic acid.

m.p. 105.5°–106.5° C.

Anal.(%); for $C_{18}H_{16}O_5S$—Calcd.: C, 62.78; H, 4.68. Found: C, 62.86; H, 4.70.

EXAMPLE 2

(1) 5.52 g of 4-methylbiphenyl ether and 2.99 g of maleic anhydride were dissolved in 200 ml of dichloromethane. 5.97 g of anhydrous aluminum chloride were added to the solution, little by little, under ice-cooling and with stirring, then the mixture was stirred at room temperature for 5 hours. The reaction mixture was concentrated under reduced pressure, poured into a mixture of 5 ml of concentrated hydrochloric acid and 100 g of ice and then extracted with diethyl ether. The extract was washed with water and dried over magnesium sulfate, and the diethyl ether was removed by evaporation under reduced pressure. The residue was recrystallized from a mixture of hexane and acetone to give 4.58 g of 3-[4-(4-methylphenoxy)benzoyl]acrylic acid.

m.p. 145°–146° C.

(2) The procedure in Example 1 was followed, except that 2.82 g of 3-[4-(4-methylphenoxy)benzoyl]acrylic acid were used in place of 3-(4-phenoxybenzoyl)acrylic acid, to give 3.01 g of 2-acetylthio-3-[4-(4-methylphenoxy)benzoyl]propionic acid in the form of an oil.

IR $\nu_{max}^{neat}$ cm$^{-1}$: 1720(thioester), 1710(carboxylic acid), 1680 (ketone)

$^1$H-NMR(CDCl$_3$), ppm: δ=2.36(3H, s), 2.38(3H, s), 3.55(1H, dd, J=16 Hz, 4 Hz), 3.67(1H, dd, J=16 Hz, 6 Hz), 4.60(1H, bs), 4.77(1H, dd, J=6 Hz, 4 Hz), 6.94–7.30(6H, m), 7.91(2H, d, J=8 Hz)

EXAMPLE 3

(1) The procedure in Example 2(1) was followed, except that 6.36 g of 4-isopropylbiphenyl ether were used in place of 4-methylbiphenyl ether, to give 5.22 g of 3-[4-(4-isopropylphenoxy)benzoyl]acrylic acid.

m.p. 133°–134.5° C.

(2) The procedure in Example 1 was followed, except that 3.10 g of 3-[4-(4-isopropylphenoxy)benzoyl]acrylic acid were used in place of 3-(4-phenoxybenzoyl)acrylic acid, to give 1.50 g of 2-acetylthio-3-[4-(4-isopropylphenoxy)benzoyl]-propionic acid.

m.p. 110°–111.5° C.

Anal.(%); for $C_{21}H_{22}O_5S$—Calcd.: C, 65.27; H, 5.74. Found: C, 65.45; H, 5.81.

EXAMPLE 4

(1) The procedure in Example 2(1) was followed, except that 6.00 g of 4-methoxybiphenyl ether were used in place of 4-methylbiphenyl ether, to give 3.13 g of 3-[4-(4-methoxyphenoxy)benzoyl]acrylic acid.

m.p. 137°–139° C.

(2) The procedure in Example 1 was followed, except that 2.98 g of 3-[4-(4-methoxyphenoxy)benzoyl]acrylic acid were used in place of 3-(4-phenoxybenzoyl)acrylic acid, to give 2.55 g of 2-acetylthio-3-[4-(4-methoxyphenoxy)benzoyl]propionic acid.

m.p. 110°–111° C.

Anal.(%); for $C_{19}H_{18}O_6S$—Calcd.: C, 60.95; H, 4.85. Found: C, 61.11; H, 4.86.

EXAMPLE 5

(1) The procedure in Example 2(1) was followed, except that 6.14 g of 2-chlorobiphenyl ether were used in place of 4-methylbiphenyl ether, to give 5.29 g of 3-[4-(2-chlorophenoxy)benzoyl]acrylic acid.

m.p. 145°–147° C.

(2) The procedure in Example 1 was followed, except that 3.03 g of 3-[4-(2-chlorophenoxy)benzoyl]acrylic acid and 30 ml of chloroform were used in place of 3-(4-phenoxybenzoyl)acrylic acid and diethyl ether, respectively, to give 3.22 g of 2-acetylthio-3-[4-(2-chlorophenoxy)benzoyl]propionic acid.

IR $\nu_{max}^{CHCl_3}$ cm$^{-1}$: 1720–1680 (carbonyl)

$^1$H-NMR(CDCl$_3$), ppm: δ=2.38(3H, s), 3.55(1H, dd, J=16 Hz, 6 Hz), 3.67(1H, dd, J=16 Hz, 7 Hz), 4.76(1H, dd, J=7 Hz, 6 Hz), 6.96(2H, d, J=8 Hz), 7.13(1H, d, J=8 Hz), 7.15–7.36(2H, m), 7.51(1H, d, J=8 Hz), 7.94(2H, d, J=8 Hz), 8.46(1H, s)

EXAMPLE 6

(1) The procedure in Example 2(1) was followed, except that 6.14 g of 3-chlorobiphenyl ether were used in place of 4-methylbiphenyl ether, to give 3.78 g of 3-[4-(3-chlorophenoxy)benzoyl]acrylic acid.

m.p. 110°–111° C.

(2) The procedure in Example 1 was followed, except that 3.03 g of 3-[4-(3-chlorophenoxy)benzoyl]acrylic acid and 30 ml of dichloromethane were used in place of 3-(4-phenoxybenzoyl)acrylic acid and diethyl ether, respectively, to give 3.14 g of 2-acetylthio-3-[4-(3-chlorophenoxy)benzoyl]propionic acid.

m.p. 122°–125° C.

Anal.(%); for $C_{18}H_{15}ClO_5S$—Calcd.: C, 57.07; H, 3.99. Found: C, 57.15; H, 4.09.

EXAMPLE 7

The procedure in Example 1 was followed, except that 3-[4-(4-chlorophenoxy)benzoyl]acrylic acid was used in place of 3-(4-phenoxybenzoyl)acrylic acid, to give 3.50 g of 2-acetylthio-3-[4-(4-chlorophenoxy)benzoyl]propionic acid.

m.p. 91°–94° C.

Anal.(%); for $C_{18}H_{15}ClO_5S$—Calcd.: C, 57.07; H, 3.99. Found: C, 57.18; H, 4.10.

EXAMPLE 8

(1) The procedure in Example 2(1) was followed, except that 7.47 g of 4-bromobiphenyl ether were used in place of 4-methylbiphenyl ether, to give 6.86 g of 3-[4-(4-bromophenoxy)benzoyl]acrylic acid.

m.p. 171°–172° C.

(2) The procedure in Example 1 was followed, except that 3.47 g of 3-[4-(4-bromophenoxy)benzoyl]acrylic acid and 30 ml of chloroform were used in place of 3-(4-phenoxybenzoyl)acrylic acid and diethyl ether, respectively, to give 4.15 g of 2-acetylthio-3-[4-(4-bromophenoxy)benzoyl]propionic acid.

m.p. 117°–118° C.

Anal.(%); for $C_{18}H_{15}BrO_5S$—Calcd.: C, 51.08; H, 3.57. Found: C, 51.14; H, 3.61.

EXAMPLE 9

(1) The procedure in Example 2(1) was followed, except that 7.17 g of 3,4-dichlorobiphenyl ether were used in place of 4-methylbiphenyl ether, to give 5.56 g of 3-[4-(3,4-dichlorophenoxy)benzoyl]acrylic acid.

m.p. 155°–156.5° C.

(2) The procedure in Example 1 was followed, except that 3.37 g of 3-[4-(3,4-dichlorophenoxy)benzoyl]acrylic acid and 30 ml of dichloromethane were used in placed of 3-(4-phenoxybenzoyl)acrylic acid and diethyl ether, respectively, to give 3.96 g of 2-acetylthio-3-[4-(3,4-dichlorophenoxy)benzoyl]-propionic acid in the form of an oil.

IR $\nu_{max}^{CHCl_3}$ cm$^{-1}$: 1750–1670 (carbonyl)

$^1$H-NMR(CDCl$_3$), ppm: δ=2.40(3H, s), 3.55(1H, dd, J=16 Hz, 4 Hz), 3.70(1H, dd, J=16 Hz, 6 Hz), 4.78(1H, dd, J=6 Hz, 4 Hz), 6.70(1H, bs), 6.90–7.52(5H, m), 7.92(2H, d)

EXAMPLE 10

(1) The procedure in Example 2(1) was followed, except that 6.56 g of 4-chloro-2-methylbiphenyl ether were used in place of 4-methylbiphenyl ether, to give 8.64 g of 3-[4-(4-chloro-2-methylphenoxy)benzoyl]acrylic acid.

m.p. 138°–139° C.

(2) The procedure in Example 1 was followed, except that 3.17 g of 3-[4-(4-chloro-2-methylphenoxy)benzoyl]acrylic acid were used in place of 3-(4-phenoxybenzoyl)acrylic acid, to give 3.60 g of 2-acetylthio-3-[4-(4-chloro-2-methylphenoxy)-benzoyl]propionic acid in the form of an oil.

IR $\nu_{max}^{neat}$ cm$^{-1}$: 1740–1680 (carbonyl)
$^1$H-NMR(CDCl$_3$), ppm: $\delta$=2.17(3H, s), 2.39(3H, s), 3.57(1H, dd, J=18 Hz, 5 Hz), 3.66(1H, dd, J=18 Hz, 8 Hz), 4.77(1H, dd, J=8 Hz, 5 Hz), 6.93(3H, m), 7.18–7.34(2H, m), 7.94(2H, d, J=9 Hz), 8.54(1H, bs)

EXAMPLE 11

(1) The procedure in Example 2(1) was followed, except that 6.56 g of 4-chloro-3-methylbiphenyl ether were used in place of 4-methylbiphenyl ether, to give 7.07 g of 3-[4-(4-chloro-3-methylphenoxy)benzoyl]acrylic acid.

m.p. 135°–136.5° C.

(2) The procedure in Example 1 was followed, except that 3.17 g of 3-[4-(4-chloro-3-methylphenoxy)benzoyl]acrylic acid and 30 ml of dichloromethane were used in place of 3-(4-phenoxybenzoyl)acrylic acid and diethyl ether, respectively, to give 3.83 g of 2-acetylthio-3-[4-(4-chloro-3-methylphenoxy)benzoyl]propionic acid in the form of an oil.

IR $\nu_{max}^{neat}$ cm$^{-1}$: 1720–1680 (carbonyl)
$^1$H-NMR(CDCl$_3$), ppm: $\delta$=2.36(3H, s), 2.38(3H, s), 3.52(1H, dd, J=16 Hz, 4 Hz), 3.67(1H, dd, J=16 Hz, 6 Hz), 4.75(1H, dd, J=6 Hz, 4 Hz), 5.30(1H, bs), 6.80–7.02(4H, m), 7.36(1H, d, J=8 Hz), 7.93(2H, d, J=8 Hz)

EXAMPLE 12

(1) 5.36 g of 3-(4-phenoxybenzoyl)acrylic acid were dissolved in 30 ml of dimethylformamide, then 1.48 g of lithium carbonate and 5.68 g of methyl iodide were added. The mixture was stirred at room temperature for 3 hours and then allowed to stand overnight. Diethyl ether was added to the reaction mixture, which was then washed, in turn, with water, a saturated aqueous solution of sodium hydrogencarbonate and water, and then dried over magnesium sulfate. The diethyl ether was removed by evaporation under reduced pressure, and the residue was recrystallized from a mixture of benzene and hexane to give 5.24 g of methyl 3-(4-phenoxybenzoyl)acrylate.

m.p. 88°–90° C.

(2) 2.82 g of methyl 3-(4-phenoxybenzoyl)acrylate were dissolved in 30 ml of diethyl ether, then 1.5 ml of thioacetic acid were added. The mixture was stirred for 3 hours. The reaction mixture was washed, in turn, with water, a saturated aqueous solution of sodium hydrogencarbonate and water and then dried over magnesium sulfate. The diethyl ether was removed by distillation under reduced pressure. The residue was purified first by silica gel column chromatography, eluted with a mixture of hexane and diethyl ether, then by recrystallization from a mixture of hexane and diethyl ether to give 2.91 g of methyl 2-acetylthio-3-(4-phenoxybenzoyl)-propionate.

m.p. 59°–61° C.

Anal.(%); for C$_{19}$H$_{18}$O$_5$S—Calcd: C, 63.67; H, 5.06. Found: C, 63.49; H, 5.12.

EXAMPLE 13

(1) 5.36 g of 3-(4-phenoxybenzoyl)acrylic acid were dissolved in 30 ml of dimethylformamide, and then 1.36 g of potassium carbonate and 3.08 g of diethyl sulfate were added. The mixture was stirred at room temperature for 3 hours. Diethyl ether was added to the reaction mixture, which was then washed, in turn, with water, a saturated aqueous solution of sodium hydrogencarbonate and water, and dried over magnesium sulfate. The diethyl ether was removed by evaporation under reduced pressure. The residue was purified first by silica gel column chromatography, eluted with a mixture of hexane and diethyl ether, then by recrystallization from hexane to give 4.36 g of ethyl 3-(4-phenoxybenzoyl)acrylate.

m.p. 50°–53.5° C.

(2) The procedure in Example 12(2) was followed, except that 2.96 g of ethyl 3-(4-phenoxybenzoyl)acrylate was used in place of methyl 3-(4-phenoxybenzoyl)acrylate, to give 3.46 g of ethyl 2-acetylthio-3-(4-phenoxybenzoyl)propionate.

m.p 78°–79° C.

Anal.(%); for C$_{20}$H$_{20}$O$_5$S—Calcd.: C, 64.50; H, 5.41. Found: C, 64.53; H, 5.52.

EXAMPLE 14

(1) 6.24 g of isopropyl 3-(4-phenoxybenzoyl)propionate were dissolved in 50 ml of chloroform. After a catalytic amount of anhydrous aluminum chloride was added, a solution of 3.62 g of bromine in 20 ml of chloroform was added dropwise over 30 minutes. The reaction mixture was washed with water, then dried over magnesium sulfate. The chloroform was removed by evaporation under reduced pressure to give oily isopropyl 3-bromo-3-(4-phenoxybenzoyl)propionate, which was dissolved, without purification, in 50 ml of dimethylformamide. 3.02 g of potassium acetate were added under ice-cooling, and the mixture was stirred for 30 minutes. Diethyl ether was added to the reaction mixture, which was then washed with water and dried over magnesium sulfate. The diethyl ether was distilled off under reduced pressure and the residue was recrystallized from a mixture of hexane and diethyl ether to give 5.83 g of isopropyl 3-(4-phenoxybenzoyl)acrylate.

m.p. 71.5°–72° C.

(2) The procedure in Example 12(2) was follows, except that 3.10 g of isopropyl 3-(4-phenoxybenzoyl)acrylate were used in place of methyl 3-(4-phenoxybenzoyl)acrylate, to give 3.62 g of isopropyl 2-acetylthio-3-(4-phenoxybenzoyl)-propionate in the form of an oil.

IR $\nu_{max}^{neat}$ cm$^{-1}$: 1730 (ester, thioester) 1690 (ketone)
$^1$H-NMR(CDCl$_3$), ppm: $\delta$=1.22(3H, d, J=6 Hz), 1.25(3H, d, J=6 Hz), 2.37(3H, s), 3.51(1H, dd, J=17 Hz, 4 Hz), 3.66(1H, dd, J=17 Hz, 8 Hz), 4.67(1H, dd, J=8 Hz, 4 Hz), 5.05(1H, heptet, J=6 Hz), 6.96–7.48(7H, m), 8.01(2H, d, J=8 Hz)

EXAMPLE 15

(1) The procedure in Example 14(1) was followed, except that 6.80 g of pentyl 3-(4-phenoxybenzoyl)propionate were used in place of isopropyl 3-(4-phenoxybenzoyl)propionate, to give 6.39 g of pentyl 3-(4-phenoxybenzoyl)acrylate in the form of an oil.

$^1$H-NMR(CDCl$_3$), ppm: $\delta$=0.92(3H, m), 1.37(4H, m), 1.69(2H, m), 4.27(2H, t, J=7 Hz), 6.90(1H, d, J=16

Hz), 7.00–7.50(7H, m), 7.94(1H, d, J=16 Hz), 8.01(2H, d, J=8 Hz)

(2) The procedure in Example 12(2) was followed, except that 3.38 g of pentyl 3-(4-phenoxybenzoyl)acrylate were used in place of methyl 3-(4-phenoxybenzoyl)acrylate, to give 3.93 g of pentyl 2-acetylthio-3-(4-phenoxybenzoyl)propionate in the form of an oil.

IR $\nu_{max}^{neat}$ cm$^{-1}$: 1735 (ester, thioester) 1685 (ketone)

$^1$H-NMR(CDCl$_3$), ppm: $\delta$=0.87(3H, m), 1.30(4H, m), 1.63(2H, m), 2.38(3H, s), 3.52(1H, dd, J=18 Hz, 5 Hz), 3.66(1H, dd, J=18 Hz, 8 Hz), 4.14(2H, t, J=6 Hz), 4.72(1H, dd, J=8 Hz, 5 Hz), 6.95–7.48(7H, m), 7.94(2H, d, J=8 Hz)

EXAMPLE 16

3.58 g of 2-acetylthio-3-[4-(4-methylphenoxy)benzoyl]-propionic acid were dissolved in 50 ml of ethanol, then a solution of 0.04 g of sodium hydroxide in 10 ml of ethanol was added dropwise, under ice-cooling and with stirring. The mixture was stirred at the same temperature for a further one hour. 20 ml of diethyl ether were added to the reaction mixture and the precipitate was collected by filtration, then washed with diethyl ether, to give 3.04 g of sodium 2-acetylthio-3-[4-(4-methylphenoxy)benzoyl]propionate.

m.p. 140°–145° C. (dec.)

Anal.(%); for C$_{19}$H$_{17}$NaO$_5$S—Calcd.: C, 59.99; H, 4.50. Found: C, 59.84; H, 4.45.

EXAMPLE 17

(1) The procedure in Example 12(1) was followed, except that 5.64 g of 3-[4-(4-methylphenoxy)benzoyl]acrylic acid and 5.98 g of ethyl iodide were used in place of 3-(4-phenoxybenzoyl)acrylic acid and methyl iodide, respectively, to give 4.74 g of ethyl 3-[4-(4-methylphenoxy)benzoyl]acrylate in the form of an oil.

$^1$H-NMR(CDCl$_3$), ppm: $\delta$=1.34(3H, t, J=7 Hz), 2.37(3H, s), 4.30(2H, q, J=7 Hz), 6.88(1H, d, J=16 Hz), 6.98–7.36(6H, m), 7.90(1H, d, J=16 Hz), 7.99(2H, d, J=8 Hz)

(2) The procedure in Example 12(2) was followed, except that 3.10 g of ethyl 3-[4-(4-methylphenoxy)benzoyl]acrylate were used in place of methyl 3-(4-phenoxybenzoyl)acrylate, to give 3.18 g of ethyl 2-acetylthio-3-[4-(4-methylphenoxy)-benzoyl]propionate.

m.p. 85°–86.5° C.

Anal.(%); for C$_{21}$H$_{22}$O$_5$S—Calcd.: C, 65.27; H, 5.74. Found: C, 65.29; H, 5.71.

EXAMPLE 18

(1) The procedure in Example 17(1) was followed, except that 6.20 g of 3-[4-(4-isopropylphenoxy)benzoyl]acrylic acid were used in place of 3-[4-(4-methylphenoxy)benzoyl]acrylic acid, to give 4.91 g of ethyl 3-[4-(4-isopropylphenoxy)-benzoyl]acrylate in the form of an oil.

$^1$H-NMR(CDCl$_3$), ppm: $\delta$=1.29(6H, d, J=6 Hz), 1.35(3H, t, J=7 Hz), 2.96(1H, heptet, J=6 Hz), 4.32(2H, q, J=7 Hz), 6.90(1H, d, J=16 Hz), 7.02(2H, d, J=8 Hz), 7.04(2H, d, J=8 Hz), 7.28(2H, d, J=8 Hz), 7.91(1H, d, J=16 Hz), 8.00(2H, d, J=8 Hz)

(2) The procedure in Example 12(2) was followed, except that 3.36 g of ethyl 3-[4-(4-isopropylphenoxy)benzoyl]acrylate were used in place of methyl 3-(4-phenoxybenzoyl)acrylate, to give 3.83 g of ethyl 2-acetylthio-3-[4-(4-isopropylphenoxy)-benzoyl]propionate in the form of an oil.

IR $\nu_{max}^{neat}$ cm$^{-1}$: 1730 (ester, thioester) 1680 (ketone)

$^1$H-NMR(CDCl$_3$), ppm: $\delta$=1.26(3H, t, J=7 Hz), 1.27(6H, d, J=6 Hz), 2.38(3H, s), 2.94(1H, heptet, J=6 Hz), 3.51(1H, dd, J=16 Hz, 4 Hz), 3.65(1H, dd, J=16 Hz, 6 Hz), 4.21(2H, q, J=7 Hz), 4.70(1H, dd, J=6 Hz, 4 Hz), 6.98(4H, d, J=8 Hz), 7.25(2H, d, J=8 Hz), 7.92(2H, d, J=8 Hz)

EXAMPLE 19

(1) The procedure in Example 17(1) was followed, except that 6.00 g of 3-[4-(4-methoxyphenoxy)benzoyl]acrylic acid were used in place of 3-[4-(4-methylphenoxy)benzoyl]acrylic acid, to give 5.06 g of ethyl 3-[4-(4-methoxyphenoxy)benzoyl]-acrylate in the form of an oil.

$^1$H-NMR(CDCl$_3$), ppm: $\delta$=1.31(3H, t, J=7 Hz), 3.80(3H, s), 4.26(2H, q, J=7 Hz), 6.80(1H, d, J=16 Hz), 6.86–7.30(6H, m), 7.86(1H, d, J=16 Hz), 7.93(2H, d, J=8 Hz)

(2) The procedure in Example 12(2) was followed, except that 3.29 g of ethyl 3-[4-(4-methoxyphenoxy)benzoyl]acrylate were used in place of methyl 3-(4-phenoxybenzoyl)acrylate, to give 3.87 g of ethyl 2-acetylthio-3-[4-(4-methoxyphenoxy)-benzoyl]propionate in the form of an oil.

IR $\nu_{max}^{neat}$ cm$^{-1}$: 1740–1670 (carbonyl)

$^1$H-NMR(CDCl$_3$), ppm: $\delta$=1.25(3H, t, J=7 Hz), 2.36(3H, s), 3.51(1H, dd, J=18 Hz, 5 Hz), 3.67(1H, dd, J=18 Hz, 8 Hz), 3.82(3H, s), 4.20(2H, q, J=7 Hz), 4.70(1H, dd, J=8 Hz, 5 Hz), 6.90–7.04(6H, m), 7.91(2H, d, J=9 Hz)

EXAMPLE 20

(1) The procedure in Example 17(1) was followed, except that 6.05 g of 3-[4-(2-chlorophenoxy)benzoyl]acrylic acid were used in place of 3-[4-(4-methylphenoxy)benzoyl]acrylic acid, to give 5.06 g of ethyl 3-[4-(2-chlorophenoxy)benzoyl]-acrylate in the form of an oil.

$^1$H-NMR(CDCl$_3$), ppm: $\delta$=1.32(3H, t, J=7 Hz), 4.28(2H, q, J=7 Hz), 6.81(1H, d, J=16 Hz), 6.85–7.41(4H, m), 7.87(1H, d, J=16 Hz), 7.97(2H, d, J=9 Hz)

(2) The procedure in Example 12(2) was followed, except that 3.31 g of ethyl 3-[4-(2-chlorophenoxy)benzoyl]acrlyate were used in place of methyl 3-(4-phenoxybenzoyl)acrylate, to give 3.80 g of ethyl 2-acetylthio-3-[4-(2-chlorophenoxy)-benzoyl]propionate in the form of an oil.

IR $\nu_{max}^{neat}$ cm$^{-1}$: 1740–1680 (carbonyl)

$^1$H-NMR(CDCl$_3$), ppm: $\delta$=1.25(3H, t, J=7 Hz), 2.37(3H, s), 3.52(1H, dd, J=18 Hz, 5 Hz), 3.68(1H, dd, J=18 Hz, 8 Hz), 4.21(2H, q, J=7 Hz), 4.71(1H, dd, J=8 Hz, 5 Hz), 6.94(2H, d, J=9 Hz), 7.13(1H, d, J=8 Hz), 7.15–7.37(2H, m), 7.52(1H, d, J=8 Hz), 7.95(2H, d, J=9 Hz)

EXAMPLE 21

(1) The procedure in Example 17(1) was followed, except that 6.05 g of 3-[4-(3-chlorophenoxy)benzoyl]acrylic acid were used in place of 3-[4-(4-methylphenoxy)benzoyl]acrylic acid, to give 5.78 g of ethyl 3-[4-(3-chlorophenoxy)benzoyl]acrylate in the form of an oil.

$^1$H-NMR(CDCl$_3$), ppm: $\delta$=1.36(3H, t, J=7 Hz), 4.32(2H, q, J=7 Hz) 6.91(1H, d, J=16 Hz), 6.99(1H, d, J=8 Hz), 7.10(2H, d, J=8 Hz), 7.11(1H, d, J=8 Hz), 7.21(1H, d, J=8 Hz), 7.33(1H, q, J=8 Hz), 7.91(1H, d, J=16 Hz), 8.04(2H, d, J=8 Hz)

(2) The procedure in Example 12(2) was followed, except that 3.31 g of ethyl 3-[4-(3-chlorophenoxy)benzoyl]acrylate were used in place of methyl 3-(4-phenoxybenzoyl)acrylate, to give 3.83 g of ethyl 2-acetylthio-3-[4-(3-chlorophenoxy)-benzoyl]propionate in the form of an oil.

IR $\nu_{max}^{CHCl_3}$ cm$^{-1}$: 1750–1670 (carbonyl)

$^1$H-NMR(CDCl$_3$), ppm: $\delta$=1.27(3H, t, J=7 Hz), 2.39(3H, s), 3.53(1H, dd, J=16 Hz, 4 Hz), 3.69(1H, dd, J=16 Hz, 6 Hz), 4.23 (2H, q, J=7 Hz), 4.72(1H, dd, J=6 Hz, 4 Hz), 6.90–7.40(6H, m), 7.98(2H, d, J=8 Hz)

EXAMPLE 22

(1) The procedure in Example 13(1) was followed, except that 6.05 g of 3-[4-(4-chlorophenoxy)benzoyl]acrylic acid were used in place of 3-(4-phenoxybenzoyl)acrylic acid, to give 5.51 g of ethyl 3-[4-(4-chlorophenoxy)benzoyl]acrylate.

m.p. 57°–58° C.

(2) The procedure in Example 12(2) was followed, except that 3.31 g of ethyl 3-[4-(4-chlorophenoxy)benzoyl)]acrylate were used to place of methyl 3-(4-phenoxybenzoyl)acrylate, to give 3.81 g of ethyl 2-acetylthio-3-[4-(4-chlorophenoxy)-benzoyl]propionate.

m.p. 75.5°–77° C.

Anal.(%); for C$_{20}$H$_{19}$ClO$_5$S—Calcd.: C, 59.04; H, 4.71. Found: C, 58.91; H, 4.72.

EXAMPLE 23

(1) The procedure in Example 17(1) was followed, except that 6.92 g 3-[4-(4-bromophenoxy)benzoyl]acrylic acid were used in place of 3-[4-(4-methylphenoxy)benzoyl]acrylic acid, to give 6.00 g of ethyl 3-[4-(4-bromophenoxy)benzoyl]acrylate in the form of an oil.

$^1$H-NMR(CDCl$_3$), ppm: $\delta$=1.30(3H, t, J=7 Hz), 4.27(2H, q, J=7 Hz), 6.81(1H, d, J=16 Hz), 6.90–7.55(6H, m), 7.85(1H, d, J=16 Hz), 7.95(2H, d, J=9 Hz)

(2) The procedure in Example 12(2) was followed, except that 3.74 g of ethyl 3-[4-(4-bromophenoxy)benzoyl]acrylate were used in place of methyl 3-(4-phenoxybenzoyl)acrylate, to give 3.51 g of ethyl 2-acetylthio-3-[4-(4-bromophenoxy)-benzoyl]propionate.

m.p. 67°–68.5° C.

Anal.(%); for C$_{20}$H$_{19}$BrO$_5$S—Calcd.: C, 53.22; H, 4.24. Found: C, 53.34; H, 4.32.

EXAMPLE 24

(1) The procedure in Example 17(1) was followed, except that 6.74 g of 3-[4-(3,4-dichlorophenoxy)benzoyl]acrylic acid were used in place of 3-[4-(4-methylphenoxy)benzoyl]acrylic acid, to give 5.42 g of ethyl 3-[4-(3,4-dichlorophenoxy)-benzoyl]acrylate.

m.p. 115°–117° C.

(2) The procedure in Example 12(2) was followed, except that 3.65 g of ethyl 3-[4-(3,4-dichlorophenoxy)-benzoyl]-acrylate were used in place of methyl 3-(4-phenoxybenzoyl)-acrylate, to give 3.90 g of ethyl 2-acetylthio-3-[4-(3,4-dichlorophenoxy)benzoyl]propionate in the form of an oil.

IR $\nu_{max}^{CHCl_3}$ cm$^{-1}$: 1750–1670 (carbonyl)

$^1$H-HMR(CDCl$_3$), ppm: $\delta$=1.27(3H, t, J=7 Hz), 2.18(3H, s), 3.52(1H, dd, J=16 Hz, 4 Hz), 3.70(1H, dd, J=16 Hz, 6 Hz), 4.23 (2H, q, J=7 Hz), 4.72(1H, dd, J=6 Hz, 4 Hz), 6.93(1H, dd, J=8 Hz, 3 Hz), 7.04(2H, d, J=8 Hz), 7.18(1H, d, J=3 Hz), 7.47(1H, d, J=8 Hz), 7.98(2H, d, J=8 Hz)

EXAMPLE 25

3.44 g of 2-acetylthio-3-(4-phenoxybenzoyl)propionic acid were dissolved in 50 ml of dioxane, then 5 ml of distilled water and 2 ml of concentrated sulfuric acid were added, and the mixture was refluxed for 3 hours. The dioxane was removed by evaporation under reduced pressure. Diethyl ether was added to the residue, which was extracted with a saturated aqueous solution of sodium hydrogencarbonate. The extract was washed with diethyl ether, made slightly acidic by addition of dilute hydrochloric acid, and extracted with diethyl ether. The diethyl ether layer was washed with water and dried over magnesium sulfate. The diethyl ether was distilled off and the residue was purified by first by silica gel column chromatography, eluted with a mixture of hexane and dichloromethane, and then by re-crystallization from a mixture of hexane and acetone to give 1.16 g of 2-mercapto-3-(4-phenoxybenzoyl)propionic acid.

m.p. 134°–135° C.

Anal.(%); for C$_{16}$H$_{14}$O$_4$S—Calcd.: C, 63.56; H, 4.67. Found: C, 63.54; H, 4.70.

EXAMPLE 26

3.72 g of ethyl 2-acetylthio-3-(4-phenoxybenzoyl)-propionate were dissolved in 30 ml of ethanol, then 3 ml of distilled water and 1.2 ml of concentrated sulfuric acid were added, and the mixture was refluxed for 4 hours. The ethanol was removed by evaporation under reduced pressure. Diethyl ether was added to the residue, which was washed with water and dried over magnesium sulfate. The diethyl ether was distilled off and the residue was purified first by silica gel column chromatography, eluted with a mixture of hexane and diethyl ether, then by recrystallization from a mixture of hexane and diethyl ether to give 2.71 g of ethyl 2-mercapto-3-(4-phenoxybenzoyl)propionate.

m.p. 46°–47.5° C.

Anal.(%); for C$_{18}$H$_{18}$O$_4$S—Calcd.: C, 65.43; H, 5.49. Found: C, 65.46; H, 5.56.

EXAMPLE 27

The procedure in Example 26 was followed, except that 4.07 g of ethyl 2-acetylthio-3-[4-(4-chlorophenoxy)benzoyl]-propionate were used in place of ethyl 2-acetylthio-3-(4-phenoxybenzoyl)propionate, to give 2.77 g of ethyl 3-[4-(4-chlorophenoxy)benzoyl]-2-mercaptopropionate.

m.p. 75.5°–76.5° C.

Anal.(%); for C$_{18}$H$_{17}$ClO$_4$S—Calcd.: C, 59.26; H, 4.70. Found: C, 59.14; H, 4.76.

EXAMPLE 28

3.30 g of ethyl 2-mercapto-3-(4-phenoxybenzoyl)-propionate were dissolved in 40 ml of diethyl ether, then 0.5 ml of pyridine and 3.0 ml of propionyl chloride were added. The mixture was stirred at room temperature for 5 hours and then allowed to stand overnight. The reaction mixture was washed, in turn, with water, a saturated aqueous solution of sodium hydrogencarbonate and water, dried over magnesium sulfate, and the diethyl ether was distilled off. The residue was purified first by silica gel column chromatography, eluted with a mixture of hexane and diethyl ether, then by recrystallization from a mixture of hexane and diethyl ether to give 3.45 g of ethyl 3-(4-phenoxybenzoyl)-2-propionylthiopropionate.

m.p. 55°–57° C.

Anal.(%); for $C_{21}H_{22}O_5S$—Calc.: C, 65.27; H, 5.74. Found: C, 65.29; H, 5.69.

EXAMPLE 29

The procedure in Example 28 was followed, except that 3.0 ml of isobutyryl chloride were used in place of propionyl chloride, to give 3.88 g of ethyl 2-isobutyrylthio-3-(4-phenoxybenzoyl)propionate in the form of an oil.

IR $\nu_{max}^{neat}$ cm$^{-1}$: 1735 (ester, thioester) 1680 (ketone)

$^1$H-NMR(CDCl$_3$), ppm: δ=1.26(9H, m), 2.79(1H, heptet, J=6 Hz), 3.52(1H, dd, J=17 Hz, 5 Hz), 3.68(1H, dd, J=17 Hz, 8 Hz), 4.22(2H, q, J=7 Hz), 4.70(1H, dd, J=8 Hz, 5 Hz), 6.98–7.48(7H, m), 7.96(2H, d, J=8 Hz)

EXAMPLE 30

The procedure in Example 28 was followed, except that 3.0 ml of hexanoyl chloride were used in place of propionyl chloride, to give 3.30 g of ethyl 2-hexanoylthio-3-(4-phenoxybenzoyl)propionate in the form of an oil.

IR $\nu_{max}^{neat}$ cm$^{-1}$: 1735 (ester, thioester) 1680 (ketone)

$^1$H-NMR(CDCl$_3$), ppm: δ=0.89(3H, m), 1.27(3H, t, J=7 Hz), 1.30(4H, m), 1.69(2H, m), 2.60(2H, t, J=7 Hz), 3.51(1H, dd, J=17 Hz, 4 Hz), 3.67(1H, dd, J=17 Hz, 8 Hz), 4.22(2H, q, J=7 Hz), 4.72(1H, dd, J=8 Hz, 4 Hz), 6.96–7.48(7H, m), 7.95(2H, d, J=9 Hz)

EXAMPLE 31

The procedure in Example 13(2) was followed, except that 2.22 g of thiobenzoic acid were used in place of thioacetic acid, to give 4.02 g of ethyl 2-benzoylthio-3-(4-phenoxybenzoyl)propionate.

m.p. 95°–96° C.

Anal.(%); for $C_{25}H_{22}O_5S$—Calcd.: C, 69.11; H, 5.10. Found: C, 69.02; H, 5.15.

What we claim is:

1. 3-benzoyl-2-mercaptopropionic acid derivatives having the formula:

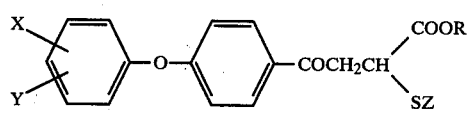

wherein X is hydrogen or halogen, Y is hydrogen, halogen, methoxy or alkyl having 1 to 3 carbon atoms, Z is hydrogen, alkylcarbonyl having 2 to 6 carbon atoms or benzoyl, and R is hydrogen, alkali metal or alkyl having 1 to 5 carbon atoms.

2. A compound according to claim 1 wherein X is hydrogen.

3. A compound according to claim 1 wherein Y is hydrogen or halogen.

4. A compound according to claim 1 wherein Z is acetyl.

5. A compound according to claim 1 wherein R is hydrogen or ethyl.

6. A compound according to claim 1 wherein X is hydrogen, Y is hydrogen or halogen, Z is acetyl and R is hydrogen or ethyl.

* * * * *